US00PP09060P

United States Patent [19]

Tobutt

[11] Patent Number: Plant 9,060

[45] Date of Patent: Feb. 21, 1995

[54] COLUMNAR APPLE TREE — OBELISK VARIETY

[75] Inventor: Kenneth R. Tobutt, Maidstone, United Kingdom

[73] Assignee: Horticulture Research International, Warwick, United Kingdom

[21] Appl. No.: 179,312

[22] Filed: Jan. 10, 1994

[51] Int. Cl.[6] ..... A01H 5/00
[52] U.S. Cl. ..... Plt./34.1
[58] Field of Search ..... Plt. 34.1

*Primary Examiner*—James R. Feyrer
*Attorney, Agent, or Firm*—Burns, Doane, Swecker & Mathis

[57] ABSTRACT

A new and distinct variety of apple tree having weak to medium vigor is provided which exhibits a columnar growth habit that generally resembles a vertical pole. The new variety resulted from a cross between a plant designated A1583 that was produced by the crossing of the COX'S ORANGE PIPPIN and COURT PENDU PLAT varieties (non-patented in the U.S.) and the WIJCIK variety (U.S. Plant Pat. No. 4,382). Flowers form later than on the other varieties of columnar apple trees. The new variety forms attractive small to medium sized fruit having a yellow ground color with a high level of red-purple overcolor. The overall appearance is a rich maroon red with some light green or yellow coloration depending upon the degree of ripeness. The fruit configuration is somewhat asymmetric and generally is regular, flat-round to round. The fruit flesh is white and generally remains crisp and rather brisk until the end of the calendar year when properly stored. The harvest date typically is early October. The fruit commonly can be cold-stored until April while present in a ambient atmosphere.

1 Drawing Sheet

SUMMARY OF THE INVENTION

The new variety of apple tree was created in the course of a planned plant breeding program that was initiated during 1970 at the East Malling Research Station of The Kent Incorporated Society for Promoting Experiments in Horticulture at East Malling, Maidstone, Kent, England. The female parent (i.e., the seed parent) was designated A1583 and was the product of the crossing of the COX'S ORANGE PIPPIN and COURT PENDU PLAT varieties (non-patented in the U.S.) and the male parent (i.e., pollen parent) was the WIJCIK variety (U.S. Plant Pat. No. 4,382). The parentage of the new variety can be summarized as follows:

(COX'S ORANGE PIPPIN×COURT PENDU PLAT)×WIJCIK.

The seeds resulting from this pollination were sown and plants were obtained that were physically and biologically different from each other. Selective study resulted in the identification of a single plnat of the new variety. The new variety of the present invention initially was designated SA 54/81.

It was found that the new apple variety of the present invention possesses the following combination of characteristics:

(a) exhibits a columnar growth habit,
(b) commonly exhibits weak to medium vigor which is more than that exhibited by the TELAMON and CHARLOTTE varieties, and less than that exhibited by the TUSCAN variety,
(c) flowers later than other previously available columnar apple varieties,
(d) forms attractive small to medium sized fruit having a yellow ground color with a high degree of somewhat striped rich maroon red overcolor that commonly can be cold-stored until approximately April while present in an ambient atmosphere, and
(e) commonly exhibits an early October harvest date.

The late flowering of the new variety in the United Kingdom generally corresponds to that of the GALA variety (U.S. Plant Pat. No. 3,637) and the GOLDEN DELICIOUS variety (non-patent in the U.S.). The GALA variety sometimes is known as the KIDD's D-8 variety.

When properly stored the mature fruit of the new variety tends to retain its crispness and briskness until approximately the end of the calendar year, and tends to mellow upon the passage of time in the following New Year.

The columnar growth habit combined with the attractive yellow with red-purple overcolored fruit is particularly striking. Side branches are very limited. When side branches occur, they can be readily removed with secateurs. The axillary buds tend to form on fruit-bearing spurs rather than on extension shoots. The flowers and fruit tend to form along a single main branch or central leader (as illustrated). The distinctive growth habit of the new variety makes possible very dense planting. Rows of trees of the new variety form sturdy natural cordons. However, in extremely windy areas it may be desirable to at least partially shelter the trees from wind with approximate wind barriers. The trees of the new variety are relatively easy to manage and require little pruning. It has been found that pruning of the terminal bud does not induce typical branching. For instance, following such pruning 1 to 3 buds near the top of the remaining trunk commonly will break and will grow up vertically to replace the leader and a few shoots further down the tree may also form. The trunk commonly increases in girth sufficiently to allow the tree to bear an unthinned heavy crop of fruit. Mechanized fruit picking can be employed if desired. Additionally, the trees of the new variety can serve as spacesaving pollinators in more conventional orchards. Alternatively, the trees of the new variety can be grown for ornamental purposes in parks, gardens, and along the roadside.

The combination of characteristics exhibited by the new variety enables it to be readily distinguished from other columnar apply varieties, such as MAYPOLE (U.S. Plant Pat. No. 6,184), TELAMON (U.S. Plant Pat. No. 6,224), TUSCAN (U.S. Plant Pat. No. 6,225), TRAJAN (U.S. Plant Pat. No. 6,226), and HERCULES (U.S. Plant patent application Ser. No. 179,357, filed concurrently herewith). The HERCULES variety is known as the CHARLOTTE variety in many parts of the world.

The new variety performs well on rootstocks such as MM106. The new variety further has been evaluated during 1988–1991 at the National Fruit Trials, Brogdale Farm, Faversham, Kent, England.

The new variety has been asexually reproduced at East Malling, Maidstone, Kent, England that has included budding on MM106 rootstock. The characteristics of the new variety have been found to be stable and to be capable of transmission through succeeding generations following such propagation.

No pest and disease resistance or susceptibility for the new variety has been noted to date.

The new variety has been named the OBELISK variety. It is contemplated that the new variety will be marketed under the FLAMENCO trademark.

BRIEF DESCRIPTION OF THE PHOTOGRAPHS

The accompanying photographs show as nearly true as it is reasonably possible to make the same in color illustrations of this character, tyical specimens of the new variety while budded on MM106 rootstock. The photographs show plants being grow at East Malling, Maidstone, Kent, England. Color reference is made to The R.H.S. Colour Chart of the Royal Horticultural Society, London.

FIG. 1 illustrates three-year-old trees during May 1993. The columnar growth habit is apparent. Flowers borne on spurs primarily arising directly from the main trunk are shown particularly on the middle and right tree. The production of an occasional short side-short also is apparent. The illustrated flower petals generally are white with splashes of clear pale pink (Red Group 55D) on the upper side, and white striped with clear pale pink (Red Group 55B) on the under side.

FIG. 2 illustrates a cluster of two fruits on a spur with foliage when observed during September 1992. The configuration of typical fruit generally is shown wherein the skin coloration of the fruit is primarily a rich maroon red (approaching Greyed-Purple Group 185A) that is slightly striped or banded with the remainder being light green to yellow.

DETAILED DESCRIPTION

Figure 1:
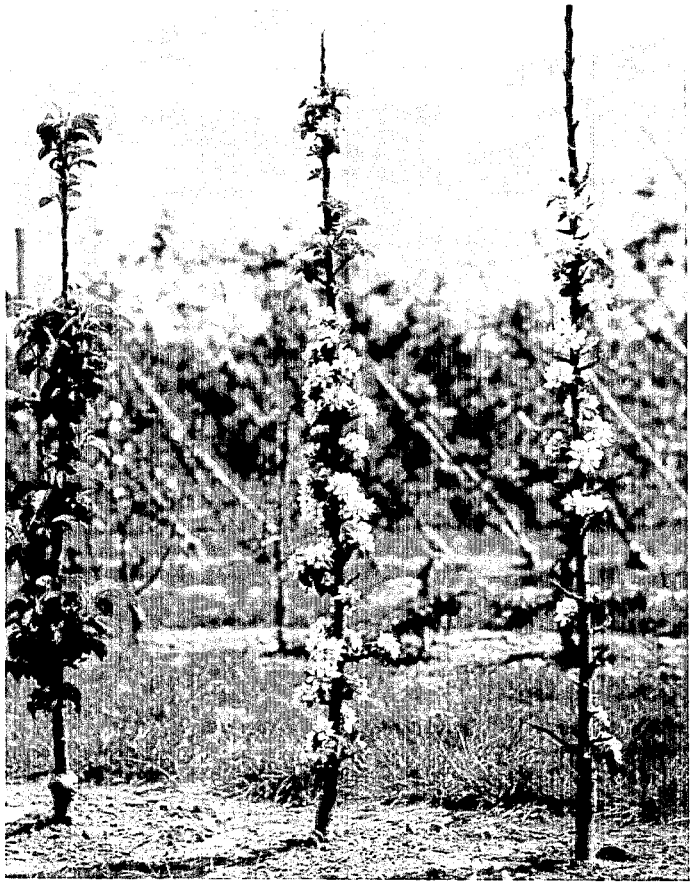
Figure 2:
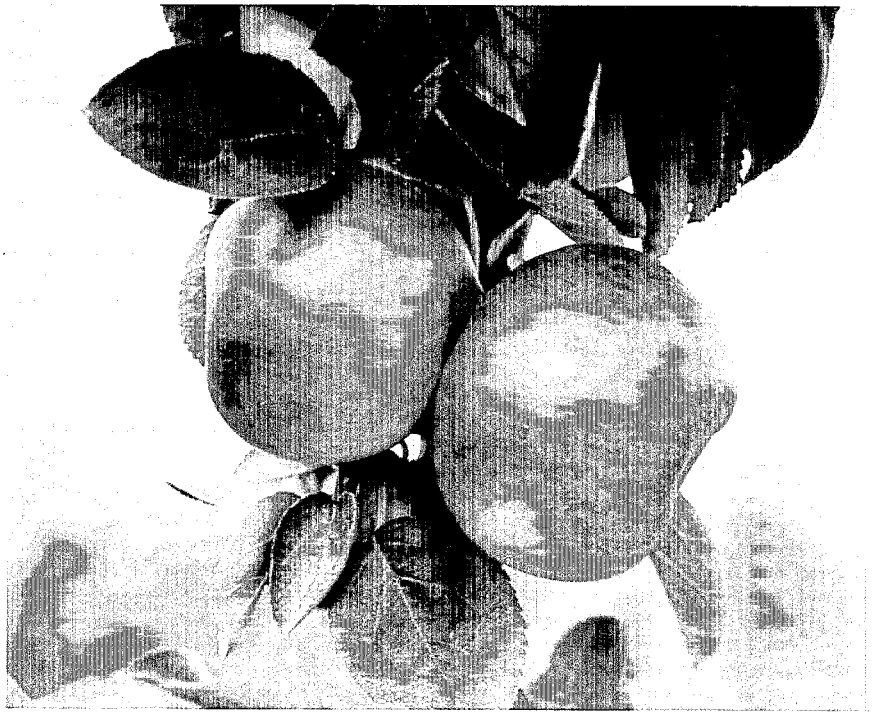

The following is a detailed description of the new OBELISK apple variety. The specimens described were grown during the 1988–1991 National Fruit Trials in England while present on MM106 rootstock. Color reference is made to The R.H.S. Colour Chart of the Royal Horticultural Society, London.

Tree:

*Habit of branches.*—Columnar, a conventional branching system along the tree truck is lacking, side branches rarely form, and commonly there is a central extension leader only.

*Growth habit.*—Short internodes. Approximately 5 internodes on average have been measured over a length of 10 cm. when observed at Cambridge, United Kingdom.

*Vigor.*—Weak to medium, more than the TELAMON and CHARLOTTE varieties, and less than the TUSCAN variety.

*Dormant one year old shoot.*—Pubescence on the upper one-half of the shoot is weak, the diameter at the center is thick, and many lenticels are present.

*Interspur length.*—Approximately 9 spurs on average have been measured over a length of 30 cm. when measured at Cambridge, United Kingdom.

*Bark.*—The current season's bark commonly is heavily pubescent and approach Grey-Brown Group 199D in coloration, and the mature bark tends to be smooth and glossy and approaches Grey-Brown Group 199A in coloration.

*Bearing habit of tree.*—Spurs low on the tree develop and continue to bear fruit as the tree gains height, and there is some tendency for bare wood to be present on the lower portion of any extension shoots that form.

*Lenticel density on bark.*—Commonly averages approximately 11.4/cm$^2$ with the actual counts commonly ranging from 8 to 15/cm$^2$.

Leaves:

*Size.*—Medium/large.

*General pose.*—Outwardly horizontal.

*Leaf blade.*—The ratio of the length to width is medium (i.e., approximately 1.5:1), commonly approximately 88 mm in length on average and approximately 60 mm in width on average, and there is only weak glossiness on the upper surfaces and weak/medium glossiness on the under surfaces. Leaf blade lengths commonly vary from approximately 82 to 93 mm., and leaf blade width commonly vary from approximately 52 to 67 mm.

*Petiole.*—Long in length, approximately 33 mm on average. Petiole lengths commonly vary from approximately 31 to 40 mm.

*Color.*—Upper surface approach Green Group 143A to 143B and lower surface approaches Yellow-Green Group 143D.

*Stipules.*—Present and commonly measure from approximately 5 to 10 mm. in length.

Flowers:

*Time of flowering.*—Later than other available columnar apple varieties in the United Kingdom, approximately at the same time as the GALA and GOLDEN DELICIOUS varieties, and approximately 7 days later than the COX'S ORANGE PIPPIN variety (e.g., May 8, 1988 vs. May 1, 1988).

*Size.*—Small, approximately 47.8 mm in diameter on average when the petals are pressed into a horizontal position.

*Petals.*—Commonly the margins are free, the upper side is white with areas of clear pale pink (Red Group 55D) and the under side is white striped with clear pale pink (Red Group 55B).

*Pollen.*—Pollen is produced; however, the new variety is self-incompatible and requires pollen from another apple variety flowering at the same time in order to set fruit.

Fruit:

*Predominance of bearing.*'On spurs.

*Size.*—Small to medium, approximately 60 to 70 mm in diameter (commonly of 67.6 mm in diameter on average and 52.5 mm in height on average).

*Shape.*—Flat globose (oblate).

*Symmetry in side view.*—Somewhat asymmetric.

*Ribbing.*—Present with very weak to weak prominence.

*Crowning at distal end.*—Present to a weak degree.

*Aperture of eye.*—Closed.

*Size of eye.*—Medium.

*Sepal length.*—Medium.

*Spacing of sepals at base.*—Generally free with some touching.

*Depth of eye basin.*—Medium deep, approximately 5.3 mm on average.

*Width of eye basin.*—medium broad, approximately 26.9 mm on average.

*Thickness of stalk.*—Medium thick.

*Length of stalk.*—Short, approximately 10.2 mm on average.

*Depth of stalk cavity.*—Medium, approximately 10.8 mm on average.

*Width of stalk cavity.*—Medium, approximately 27.1 mm on average.

*Relief of surface.*—Smooth.

*Bloom of skin.*—Absent.

*Greasiness of skin.*—Present.

*Cracking tendency of skin.*—Absent.

*Thickness of skin.*—Thin to medium.

*Ground color of skin.*—Yellow.

*Quality of overcolor.*—*High.*

*Overcolor of skin.*—Deep maroon red (as illustrated) with some banding, and with some fruits being a fairly solid deep maroon red.

*Quality of russet.*—Absent or slight.

*Location of russet.*—tends to be around stalk cavity if present.

*Size of lenticels.*—Small to medium.

*Browing of flesh* (*one hour after being cut with stainless steel knife*).—Weak.

*Firmness of flesh.*—Soft (approximately 5.5 on average when tested on penetrometer).

*Color of flesh.*—White.

*Texture of flesh.*—Fine.

*Juiciness.*—Juicy.

*Distinctness of core line median through locules*.—Weak when fruit is cut in cross-section.

*Aperture of locules.*—Open when fruit is cut in cross-section.

*Time of fruit ripening for eating.*—Late, picking commonly takes place in early October in southeast England.

The new variety forms a dessert apple having a brisk tartness which may be cold-stored (e.g., at 4° C.) until April following the harvest; however, during about January tartness commonly will begin to be lost thereby rendering the fruit less palatable and less refreshing. No commercial variety is known having a comparable flavor.

I claim:

1. A new and distinct variety of apple tree having the following combination of characteristics:

(a) exhibits a columnar growth habit, (b) commonly exhibits weak to medium vigor which is more than that exhibited by the TELAMON and CHARLOTTE varieties, and less than that exhibited by the TUSCAN variety, (c) flowers later than other previously available columnar apple varieties, (d) forms attractive small to medium sized fruit having a yellow ground color with a high degree of somewhat striped rich maroon red overcolor that commonly can be cold-stored until approximately April while present in an ambient atmosphere, and (e) commonly exhibits an early October harvest date;

substantially as herein shown and described.

* * * * *